US000001431H

United States Statutory Invention Registration [19]

[11] Reg. Number: H1431

Kern et al.

[43] Published: Apr. 4, 1995

[54] USE OF BEADS TO IMPROVE NUCLEOTIDE HYBRIDIZATION ASSAYS

[76] Inventors: David G. Kern, 5405 Quebec Common, Fremont, Calif. 94555; Patrick J. Sheridan, 2008 Horne St., San Leandro, Calif. 94578; John Todd, 1096 Orchard Rd., Lafayette, Calif. 94549

[21] Appl. No.: 971,719

[22] Filed: Nov. 4, 1992

[51] Int. Cl.[6] ..... C12Q 1/68
[52] U.S. Cl. ..... 435/6
[58] Field of Search ..... 435/6; 536/23.1

[56] References Cited

U.S. PATENT DOCUMENTS 4,898,951 2/1990 Symons ..... 548/303

OTHER PUBLICATIONS

Marko et al., Analytical Biochemistry, 128:382–387, 1982.

*Primary Examiner*—Shean Wu

[57] ABSTRACT

This invention utilizes beads in sample preparation to increase the precision of nucleotide hybridization assays.

14 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

USE OF BEADS TO IMPROVE NUCLEOTIDE HYBRIDIZATION ASSAYS

FIELD OF THE INVENTION

This invention relates to the field of medical diagnostics. More specifically, the invention relates to a method for increasing the precision of nucleotide hybridization assays by utilizing beads during sample preparation.

BACKGROUND OF THE INVENTION

Nucleotide hybridization assays are able to detect sequences of interest, by duplex formation between labeled complementary nucleic acid probes and single stranded nucleic acids targets. Typically, the probes are labeled with radioactivity or enzymes which cleave light- or color-producing molecules. The amplitude of the assay output signal can indicate either the number or merely the presence of target nucleic acids in the sample. However, the output signal is not produced solely by label probes from the formed duplexes, but also from assay imperfections, such as unduplexed label probes that were not removed. A nucleotide hybridization assay includes many steps for sample preparation and assay execution, and at each step, some amount of uncontrollable variation is produced because it is impossible to handle each sample exactly identically. Thus, when a single sample is assayed several times, the results will be variable. The best way to limit this imprecision is to minimize the number of times the sample is manipulated. However, there is a limit to the number of steps that may be eliminated.

SUMMARY OF THE INVENTION

One aspect of the invention is a method of increasing the precision of nucleotide hybridization assays by adding a bead to a liquid sample so that the pellet can be easily identified after the sample is centrifuged during sample preparation.

Another aspect of the invention is a composition of beads and target nucleic acids that are not covalently linked.

DETAILED DESCRIPTION OF THE INVENTION

A. Definitions

"Nucleotide hybridization assay" is an assay in which target nucleic acids, such as DNA, RNA, or their analogs, are detected by a labeled probe. The labeled probes can also be DNA, RNA, or their analogs.

"Target nucleic acids" can be any nucleotide sequence to be detected. For instance, the target nucleic acids can be viral in nature. Examples of such viruses of interest to be detected are Hepatitis B virus (HBV), Hepatitis C virus (HCV), Human Immunodeficiency Virus (HIV), Cytomegalovirus (CMV), etc. Target nucleic acids can also be cellular markers or genes which indicate the presence of a particular organism, such as Chlamydia.

"Labeled probes" hybridize with the target nucleic acids and contain a label, such as a radioactive atom, enzyme, or specific nucleotide sequence, which can be detected in the assay.

"Liquid sample" is any fluid biological sample to be tested which may contain the target nucleic acids to be detected. Liquid sample refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Solid material such as skin and other cells may used after solubilization.

A "bead." can be any object of solid material of appropriate density which will sediment with the target nucleic acids. The bead used will not be buoyant in the liquid sample to be assayed, and preferably, the bead will have a density similar to that of the liquid sample components to be pelleted. In general, the density will range from greater than the density of the liquid sample to similar to the density of the target nucleic acids, so that the target nucleic acids and beads pellet together under the desired centrifugation conditions. The density of the bead(s) should be different from the target nucleic acids so that they may be easily separated from one another. The density of the plurality of beads will be substantially between 0.5 to 2 g/ml when the densities of 80% of the beads are between the recited range. More preferably, the density of the beads will be substantially between 1.01 and 1.09 g/ml. Most preferably, for a viral particle, which contains the target nucleic acids, in a liquid sample of plasma, the density of the bead will about 1.05 g/ml. The composition of the bead material will be inert under the desired sample preparation conditions, so as not to interfere with the assay results. Typically a bead can comprise latex or magnetic material; polystyrene is presently preferred. The bead size and shape are not critical and may vary, but the size and shape will be chosen so they will not disrupt the detection of the target nucleic acids. Typically, the bead will be roughly spherical, and the diameter will not be smaller than 0.1 μm and no larger than 1 μm. Preferably, the diameter will be between about 0.1 and about 0.7 μm. Most preferably, the beads will be about 0.5 μm in diameter. The diameter of a plurality of beads will be substantially between 0.1 μm and 1.0 μm, for example, when the diameter of at least 80% of the beads fall between the recited range. The beads may be any color, but preferably selected for high contrast. The color red is presently a preferred embodiment.

The term "antibody" includes monoclonal antibodies, antisera, recombinant antibodies, and functional fragments thereof.

"Carder DNA" can also be added to the liquid sample to ensure that small amounts of target nucleic acids will behave predictably during sample preparation and assay steps.

Compounds are "non-convalently linked" when no covalent chemical bond exists between them. The beads serve as an indicator of, not as a carder of the target nucleic acids, and thus, no linkage between them is necessary or desired. For example, the beads are non-covalently linked when no ligand binds the target nucleic acids to the beads, for example, a biotin/avidin binding.

"Substantial sequence identity" refers to the sequence identity between a target nucleic acids and the claimed sequence, such as HBV, HCV, HIV, CMV, HTLV-1, TB, or Chlamydia. Substantial sequence identity will be at least 50%, usually, the sequence identity will be no less than 60%; more typically, the sequence identity will be no less than 75 %; preferably no less than 80%; and even more preferably at least 90%. Most preferably, the sequence identity will be at least 95 %, even more preferably at least 98 %, even more preferably at least 99 %.

"HIV" refers to the viral family known as Human Immunodeficiency Virus. Currently, it is believed that this viral family contains two major subgroups, HIV-1 and HIV-2. See Human Retroviruses and AIDS 1989, A Compilation and Analysis of Nucleic Acid and Amino Acid Sequences, edited by Gerald Myers et at., pub. Theoretical Biology and Biophysics Group, Los Alamos, New Mexico and Genbank for nucleic acid and other taxonomic features of HIV.

"HBV" refers to the viral family known as Hepatitis B Virus. See Fundamental Virology, 2nd ed., ed. Fields et al., Raven Press (1991) and Genbank for nucleic acid and other taxonomic features of HBV.

"HCV" refers to the viral family known as Hepatitis C Virus. This term includes all genotypes as well. See Houghton et at., EP 318 216; Houghton et al., EP 388 232; and Genbank for nucleic acid and other taxonomic features of HCV.

"CMV" refers to the viral family known as Cytomegalovirus. See Fundamental Virology, 2nd ed., ed. Fields et al., Raven Press (1991) and Genbank for nucleic acid and other taxonomic features of CMV.

"Chlamydia" refers to the intracellular parasitic organism *Chlamydia trachomatis.* See Review of Medical Microbiology, 17th ed., ed. Janwetz et al., pub. Appleton & Lange, Norwalk, Conn./Los Altos, Calif. (1987) and Genbank for nucleic acid and other taxonomic features.

"TB" refers the organism *Mycobacteria tuberculosis.* See Review of Medical Microbiology, 17th ed., ed. Janwetz et al., pub. Appleton & Lange, Norwalk, Conn./Los Altos, Calif. (1987) and Genbank for nucleic acid and other taxonomic features.

"HTLV-1" refers viral family known as Human T-cell Leukemia Virus, isolate 1. See Fundamental Virology, 2nd ed., ed. Fields et al., Raven Press (1991) and Genbank for nucleic acid and other taxonomic features.

B. General Methods

The first steps of a nucleotide hybridization assay include sample collection, liquification, and preparation. The beads are added to the liquid sample during sample preparation. This method of sample preparation improves the precision of the nucleotide hybridization assay.

A biological sample is collected from the subject to be tested. The sample may be blood, urine, skin, etc. If the biological sample is frozen or solid, the sample must be liquified by thawing or solubilization. If the target nucleic acids exist in small quantities, care must be taken to collect enough sample to ensure that a sufficient amount of target nucleic acids are present for detection. Next, sawnpie preparation of the liquid sample will remove contaminants and preserve and concentrate the target nucleic acids.

One step of sample preparation is centrifugation. Centrifugation facilitates easy separation of the solid material from the liquid material in a liquid sample. The beads are added before centrifuging the liquid sample. Typically, a plurality of beads will be added to the sample. If too many beads are added to the liquid sample, the resulting pellet will be difficult to resuspend. Further, if too many beads are used, then a large volume will be needed to resuspend the pellet and can cause unwanted dilution of the target nucleic acids. If too few beads are present, then the pellet will still be difficult to visualize. Depending on the beads used and the desired assay conditions, the number and volume of the beads to be used will vary. For a 1 ml liquid sample, 50 μl of 0.1% (w/v) suspension of 0.5 μm polystyrene beads is preferred. Thirty μl of this solution is not generally sufficient to visualize the pellet, and 100 μl of the bead solution would cause unnecessary dilution of the target nucleic acids. A buffer can also be added at this stage to maintain the pH level. After centrifugation, the target nucleic acids may either be found in the supernatant or the pellet depending on the sample preparation protocol and the nature of the target nucleic acids. Preferably, the target nucleic acids are deposited with the beads in the pellet after the first centrifugation. The addition of beads improves the quality of the prepared sample by helping the assay operator identify the pellet area in the tube after centrifugation. For example, if the target nucleic acids are viral in nature, these nucleotides will pellet with the beads in a first centrifugation step. The beads aid the operator in identifying the pellet with the target nucleic acids to avoid unnecessary loss of target nucleic acids. The actual pellet shape will vary greatly from sample to sample. The pellet may be spread along one side of the tube or may be localized to a small area toward the bottom of the tube. A sufficient amount of beads will allow the operator to visualize the pellet in either situation. Thus, because the pellet is easy to see, the assay operator can avoid accidently removing or disturbing the pellet. The beads may also help to lyse the cells containing the target nucleic acids.

Next, the unwanted protein and/or cell debris associated with the pelleted target nucleic acids can be degraded by adding proteinases. Carder DNA can also be added at this step to ensure predictable behavior of the target nucleic acids. When the pelleted target nucleic acids are resuspended, and the unwanted proteins are degraded, the sample is centrifuged again to pellet the remaining particulate material. Now the target nucleic acids are found in the supernatant, and visualization of the beads prevents the operator from contaminating the sample with debris from the pellet.

Now the sample is ready to be assayed. However, further steps can be taken to ensure the purity and preservation of the target nucleic acids. These steps depend on the nature of the target nucleic acids, biological sample, and nucleotide hybridization assay conditions. These steps can include adding guanidium thiocyanate to the liquid sample to preserve target nucleic acids that are RNA. Other examples of further processing steps include phenol/chloroform extraction or filtration, for concentration or purification.

One example of a nucleotide hybridization assay is described in Urdea et al., PCT WO92/02526 and Urdea et al., U.S. Pat. No. 5,124,246, and is an example of a sandwich nucleotide hybridization assay. The described assay utilizes a microtiter plate as a solid support and five sets of oligonucleotides to detect the target sequences. The five oligonucleotide sets are:

(1) plate binding oligonucleotides (oligonucleotide attached to the solid phase in Urdea et al.),
(2) capture oligonucleotides (capture probes in Urdea et al.),
(3) labeled probes (amplifier probes in Urdea et al.),
(4) branched amplifier oligonucleotides (multimer in Urdea et al.), and (5) enzyme-linked oligonucleotides (labeled oligonucleotide in Urdea et al.).

A microtiter plate is coated with the plate binding oligonucleotides (1). These plate binding oligonucleotides contain a sequence that is complementary to a sequence on the capture oligonucleotides (2). The capture oligonucleotides also comprise a second sequence that can hybridize to the target nucleic acids. Via the plate binding and capture oligonucleotides, the target nucleic acids are immobilized to the microtiter plate and separated from unwanted and unbound nucleotides by simply washing the plate.

The target nucleic acids are detected via a labeled probe (3). For this specific assay, the labeled probe comprises a region complementary to the target nucleic acids and region(s) complementary to a region on the branched amplifier oligonucleotides (4). The branched amplifier oligonucleotide comprises multiple regions, which hybridize with a region on the enzyme-linked oligonucleotides (5). The enzyme-linked oligonucleotides cleave light producing molecules that can be detected with a luminometer.

Alternatively, the polymerase chain reaction (PCR) is another well-known means for detecting small amounts of target nucleic acids. The assay is described in Mullis et al., *Meth. Enzymol.* 155:335–350 (1987); U.S. Pat. Nos. 4,683,195; and 4,683,202. This method, unfortunately, cannot quantitate the amount of target nucleic acids. Two "primer" oligonucleotides hybridize with the target nucleic acids and are used to prime the reaction. A thermostable polymerase creates copies of target nucleic acids from the primers using the original target nucleic acids as a template. After a large amount of target nucleic acids are generated by the polymerase, they can be detected by more traditional methods, such as Southern blots.

EXAMPLES

The example presented below are provided as a further guide to the practitioner of ordinary skill in the art, and are not to be construed as limiting the invention in any way.

EXAMPLE 1

Sandwich Nucleotide Hybridization Assay for HIV-1 RNA with and without Beads This example illustrates the use of the invention in an HIV-1 RNA assay.

A "15×3" sandwich nucleotide hybridization assay format was employed in this example. The "15×3" designates an assay utilizing two multimers:

(1) a labeled probe having
  (A) a first segment that binds to the HIV-1 nucleic acid in the pol region and
  (B) a second segment that binds to the first segment of a branched amplifier oligonucleotide;
(2) a branched amplifier oligonucleotide having
  (A) a first segment that hybridizes to the second segment (B) of the labeled probe;
  (B) a second segment that contains fifteen iterations of an oligonucleotide which binds to three enzyme-linked oligonucleotides.

The regions of the labeled probes and capture oligonucleotides that were HIV-specific, and their respective names as used in this assay were as follows:

HIV Labeled Probes

HIV.104 (SEQ ID NO:1)

TTCCTGGCAAAYYYATKTCTYCTAMTACT-GTAT

HIV.105 (SEQ ID NO:2)

CTCCAATTTTCCYCCTATCATTTTTGGYTT-CCATY

HIV.106 (SEQ ID NO:3)

KTATYTGATCRTAYTGTCYYACTTT-GATAAAAC

HIV.108 (SEQ ID NO:4)

GTTGACAGGYGTAGGTC-CTACYAATAYTTGTACC

HIV.110 (SEQ ID NO:5)

YTCAATAGGRCTAATKGGRAAATT-TAAAGTRCA

HIV.112 (SEQ ID NO:6)

YTCTGTCAATGGCCATTGYT-TRACYYTTGGGCC

HIV.113 (SEQ ID NO:7)

TKTACAWATYTCTRYTAATCGCTTT-TATTTTYTC

HIV.114 (SEQ ID NO:8)

AAYTYTTGAAATYTTYCCTTCCTTTT-CCATHTC

HIV.115 (SEQ ID NO:9)

AAATAYKGGAGTATTRTATGGATTYT-CAGGCCC

HIV.116 (SEQ ID NO:10)

TCTCCAYTTRGTRCTGTCYTTTTTCTT-TATRGC

HIV.117 (SEQ ID NO:11)

TYTYYTATTAAGYTCYCTGAAATCTAC-TARTTT

HIV.120 (SEQ ID NO:12)

TKTTYTAAARGGYTCYAAGATTTTTGT-CATRCT

HIV.121 (SEQ ID NO:13)

CATGTATTGATADATRAYYATKTCT-GGATGGATTTTG

HIV.122 (SEQ ID NO:14)

TATYTCTAARTCAGAYCCTACATACAAAT-CATC

HIV.123 (SEQ ID NO:15)

TCTYARYTCCTCTATTTTTGYTCTATGCT-GYYC

HIV.125 (SEQ ID NO:16)

AAGRAATGGRGGTTCTTTCTGATGYT-TYTTRTC

HIV.128 (SEQ ID NO:17)

TRGCTGCYCCATC-TACATAGAAVGTTTCTGCWC

HIV.130 (SEQ ID NO:18)

GACAACYTTYTGTCTTCCAYTGTYAGT-WASATA

HIV.132 (SEQ ID NO:19)

YGAATCCTGYAAVGCTARRT-DAATTGCTTGTAA

HIV.133 (SEQ ID NO:20)

YTGTGARTCTGTYACTATRTT-TACTTCTRRTCC

HIV.135 (SEQ ID NO:21)

TATTATTTGAYTRACWAWCTCTGATT-CACTYTK

HIV.136 (SEQ ID NO:22)

CAGRTARACYTTTTCCTTTTTTATTARYT-GYTC

HIV.137 (SEQ ID NO:23)

TCCTCCAATYCCTTTRTGTGCTGGTACC-CATGM

HIV.138 (SEQ ID NO:24)

TCCHBBACTGACTAATYTATCTACTTGTT-CATT

HIV.139 (SEQ ID NO:25)

ATCTATTCCATYYAAAAATAGYAYYT-TYCTGAT

HIV.141 (SEQ ID NO:26)

GTGGYAGRTTAAARTCAYTAGCCATTG-CTYTCC

HIV.142 (SEQ ID NO:27)

CACAGCTRGCTACTATTTCYTTYGC-TACYAYRG

HIV.144 (SEQ ID NO:28)

RYTGCCATATYCCKGGRCTACART-CTACTTGTC

HIV.145 (SEQ ID NO:29)

DGATWAYTTTTCCTCYARATGT-GTACAATCTA

HIV.146 (SEQ ID NO:30)

CTATRTAKCCACTRGCYACATGRACTG-CTACYA

HIV.147 (SEQ ID NO:31)

CYTGYCCTGTYTCTGCTGGRAT-DACTTCTGCTT

HIV.149 (SEQ ID NO:32)

TGSKGCCATTGTCTGTATGTAYTRYTKT-TACTG

HIV.151 (SEQ ID NO:33)

GAATKCCAAATTCCTGYTTRATHCCHGC-CCACC

HIV.152 (SEQ ID NO:34)

ATTYCYAYTACYCCTTGACTTTGGGGRTT-GTAGG

HIV.153 (SEQ ID NO:35)

GBCCTATRATTTKCTTTAATTCHTTATT-CATAG

HIV.154 (SEQ ID NO:36)

CTSTCTTAAGRTGYTCAGCYTGMTCTCT-TACYT

HIV.155 (SEQ ID NO:37)

TAAAATTGTGRATRAAYACTGCCATTT-GTACWG

HIV.156 (SEQ ID NO:38)

CTGCACTGTAYCCCCCAATCCC-CCYTYTTCTTT

HIV.157 (SEQ ID NO:39)

TGTCTGTWGCTATYATRYCTAYTATT-CTYTCCC

HIV.158 (SEQ ID NO:40)

TTRTRATTTGYTTTTGTARTTCTYTARTTT-GTA

HIV Capture Oligonucleotides

HIV.103 (SEQ ID NO:41)

CATCTGCTCCTGTRTCTAATAGAGCTT-CYTTTA

HIV.111 (SEQ ID NO:42)

ATCCATYCCTGGCTTTAATTTTACTG-GTACAGT

HIV.118 (SEQ ID NO:43)

TATTCCTAAYTGRACTTCCCARAARTCYT-GAGT

HIV.119 (SEQ ID NO:44)

ACWYTGGAATATYGCYGGTGATCCTTT-CCAYCC

HIV.126 (SEQ ID NO:45)

CCATTTRTCAGGRTGGAGTTCATAMC-CCATCCA

HIV.127 (SEQ ID NO:46)

CTAYTATGGGKTCYKTYTCTAACTGGTAC-CAYA

HIV.134 (SEQ ID NO:47)

ATCTGGTTGTGCTTGAATRATYCCYART-GCATA

HIV.143 (SEQ ID NO:48)

CATGCATGGCTTCYCCTTTTAGYTG-RCATTTAT

HIV.150 (SEQ ID NO:49)

AACAGGCDGCYTTAACYGTAGYACTGGT-GAAAT

HIV.159 (SEQ ID NO:50)

TGTCYCTGTAATAAACCCGAAAATTTT-GAATTT

Each labeled probe contained, in addition to the sequences substantially complementary to the HIV sequence, the following 5′ extension: AGGCATAG-GACCCGTGTCTT (SEQ ID NO:51 ). This region was complementary to a segment of the branched amplifier oligonucleotides.

Each capture oligonucleotide contained, in addition to the sequences substantially complementary to HIV-1 RNA in the pol region, the following downstream sequence complementary to plate binding oligonucleotide: CTTCTTTGGAGAAAGTGGTG (SEQ ID NO:52).

The rotor and chamber of Heraeus centrifuge were cooled to 4° C. by running the centrifuge at 100 rpm for twenty minutes at 4° C. Immediately before use, 1 ml aliquots of the clinical specimens were thawed with positive and negative controls in tap water. The liquid samples and controls were stored at room temperature until used. The Bead Suspension was vortexed. The Bead Suspension consisted of 0.1% (w/v) red polystyrene beads (0.48 μm diameter, Bangs Laboratories, #D000 480 2PR), 10 mM Tris-HCl pH 8.0, 1 mM EDTA. Fifty microliters of the Bead Suspension was added to each 1 ml liquid sample or control and then stored at room temperature until use. The liquid samples and controls were centrifuged in the Heraeus centrifuges (rotor 3753) at 23,500×g for one hour at 4° C. The liquid samples and controls were removed from the rotor and held at room temperature. Immediately after, the supernatants were removed by aspiration with care to avoid aspirating the pellet. To the pellets 220 μl Specimen Diluent (100 mM HEPES, pH 7.5; 8 mM EDTA, pH 8.0; 1.0% lithium lauryl sulfate; 12 μg/ml sonicated salmon sperm DNA; 600 mM LiCl; 638 mg/ml proteinase K; 125 fmole each capture oligonucleotides; and 250 fmole of each labeled probe) was added. After all samples received Specimen Diluent, the tubes were capped and vortexed vigorously for ten seconds.

Next, the samples and controls were incubated in a 63° C. heat block for 20 minutes to extract the pellet. After incubation, the samples and controls were vortexed vigorously for ten seconds, and then centrifuged at 23,500 x g for fifteen minutes at 25° C. After centrifugation, taking care to avoid the pellet, 200 μl of each supernatant was transferred to the appropriate wells of a microtiter plate coated with the plate binding oligonucleotides. The plate was covered with a mylar sealer. Using a plate shaker, the plate was shaken gently for thirty seconds at the lowest setting, sufficient for mixing the well contents without splashing solution on the sealer.

The plate was incubated in a plate heater at 63 ° C. for about sixteen hours. The plate was carefully removed from the heater and cooled at room temperature on the benchtop for ten minutes. The sealer was carefully removed and then discarded. All the wells were aspirated to remove the liquid and immediately filled with 400 μl Wash Buffer A (0.1% sodium dodecyl sulfate (SDS); 0.015M NaCl; and 0.0015M sodium citrate) and aspirated again. This wash step was repeated once, and all remaining liquid was aspirated from the wells before continuing. Fifty μl of branched amplifier oligonucleotides and buffer were added (30 fmole of branched amplifier oligonucleotides in 50% horse serum; 1.3 % SDS; 6 mM Tris-HCl, pH 8.0; 0.5 mg/ml proteinase K; 0.6M NaCl; and 0.06M sodium citrate) to each well. The plate was sealed with a mylar sealer, agitated for thirty seconds and incubated for thirty minutes at 45 ° C. in a plate heater.

The plate was carefully removed from the heater and cooled at room temperature for five minutes. The sealer was removed, and the wells were aspirated. Immediately after, the wells were filled with 400 μl Wash Buffer A and aspirated. This wash step was repeated once, and all remaining liquid was aspirated from the wells before continuing. Fifty/μl of enzyme-linked oligonucleotides and buffer were added (alkaline phosphatase linked oligonucleotides, disclosed in EP 883096976; 125 fmole alkaline phosphatase linked oligonucleotide in 50% horse serum; 1.3% SDS; 6 mM Tris-HCl, pH 8.0; 0.5 mg/ml proteinase K; 0.6 M NaCl; and 0.06M sodium citrate) to each well. The plate was sealed and agitated for thirty seconds. Next the plate was incubated at 45° C. in a plate heater for fifteen minutes.

The plate was carefully removed from the heater and cooled at room temperature for five minutes. The sealer was removed and the contents of the wells were aspirated. Immediately after the wells were filled with 400 μl Wash Buffer A and aspirated. This wash step was repeated once more and aspirated. Immediately after, the wells were filled with 400 μl Wash Buffer B (0.015M NaCl, 0.0015M sodium citrate) and aspirated. This wash step was repeated two more times, and all liquid was aspirated from the wells before continuing. Next, fifty μl of Lumiphos ® 530 (an enzyme-triggered dioxetane: Schaap et al., *Tet. Lett.* (1987) 28:1159–1162 and EP 254 051), obtained from Lumigen, Inc.) was added to each well. The plate was sealed and agitated for thirty seconds and incubated at 37° C. for thirty minutes. Finally, the plates were then read on a Dynatech ML 1000 luminometer. Output was given as the full integral of the light produced during the reaction.

The same samples were assayed in an identical manner except the beads were not added to the samples during sample preparation. The results of the nucleotide hybridization assay with and without the beads are presented in Tables 1 and 2 below.

TABLE 1

| | No Beads | |
|---|---|---|
| | Mean of luminescence | Coefficient of Variation (Standard Deviation/Mean) × 100% |
| Sample 1 | 4.45 | 18.4% |
| Sample 2 | 1.53 | 10.7% |
| Sample 3 | 26.71 | 15.3% |
| Sample 4 | 3.63 | 22.21% |

TABLE 2

| | With Beads | |
|---|---|---|
| | Mean of luminescence | Coefficient of Variation (Standard Deviation/Mean) × 100% |
| Sample 1 | 4.86 | 10.8% |
| Sample 2 | 1.46 | 3.4% |
| Sample 3 | 28.64 | 1.2% |
| Sample 4 | 3.68 | 12.3% |

The inclusion of beads resulted in more reproducible luminescence counts, as evidenced by the lower coefficients of variation.

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:1:

TTCCTGGCAA AYYYATKTCT YCTAMTACTG TAT 33

( 2 ) INFORMATION FOR SEQ ID NO:2:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:2:

CTCCAATTCC YCCTATCATT TTTGGYTTCC ATY 33

( 2 ) INFORMATION FOR SEQ ID NO:3:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:3:

KTATYTGATC RTAYTGTCYY ACTTTGATAA AAC 33

( 2 ) INFORMATION FOR SEQ ID NO:4:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:4:

-continued

GTTGACAGGY GTAGGTCCTA CYAATAYTGT ACC 33

( 2 ) INFORMATION FOR SEQ ID NO:5:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:5:

YTCAATAGGR CTAATKGGRA AATTTAAAGT RCA 33

( 2 ) INFORMATION FOR SEQ ID NO:6:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:6:

YTCTGTCAAT GGCCATTGYT TRACYYTTGG GCC 33

( 2 ) INFORMATION FOR SEQ ID NO:7:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:7:

TKTACA W ATY TCTRYTAATG CTTTTATTTT YTC 33

( 2 ) INFORMATION FOR SEQ ID NO:8:

( i ) SEQUENCE CHARACTERISTICS:
( A ) LENGTH: 33 nucleotides
( B ) TYPE: nucleic acid
( C ) STRANDEDNESS: single
( D ) TOPBLOGY: linear ( i i ) MOLECULE TYPE: other nucleic acid ( x i ) SEQUENCE DESCRIPTION: SEQ ID NO:8:

AAYTYTTGAA ATYTTYCCTT CCTTTTCCAT HTC 33

( 2 ) INFORMATION FOR SEQ ID NO:9:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:9:

AAATAYKGGA GTATTRTATG GATTYTCAGG CCC 3

( 2 ) INFORMATION FOR SEQ ID NO:10:

( i ) SEQUENCE CHARACTERISTICS:
( A ) LENGTH: 33 nucleotides ( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:10:

TCTCCAYTTR GTRCTGTCYT TTTTCTTTAT RGC 33

( 2 ) INFORMATION FOR SEQ ID NO:11:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:11:

TYTYYTATTA AGYTCYCTGA AATCTACTAR TTT 33

( 2 ) INFORMATION FOR SEQ ID NO:12:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:12:

TKTTYTAAAR GGYTCYAAGA TTTTTGTCAT RCT 33

( 2 ) INFORMATION FOR SEQ ID NO:13:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:13:

CATGTATTGA TADATRAYYA TKTCTGGATT TTG 33

( 2 ) INFORMATION FOR SEQ ID NO:14:

( i ) SEQUENCE CHARACTERISTICS
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:14:

TATYTCTAAR TCAGAYCCTA CATACAAATC ATC 33

( 2 ) INFORMATION FOR SEQ ID NO:15:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:15:

-continued

TCTYARYTCC TCTATTTTTG YTCTATGCTG YYC 33

( 2 ) INFORMATION FOR SEQ ID NO:16:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:16:

AAGRAATGGR GGTTCTTTCT GATGYTTYTT RTC 33

( 2 ) INFORMATION FOR SEQ ID NO:17:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:17:

TRGCTGCYCC ATCTACATAG AAVGTTTCTG C W C 33

( 2 ) INFORMATION FOR SEQ ID NO:18:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:18:

GACAACYTTY TGTCTTCCAY TGTYAGT W AS ATA 33

( 2 ) INFORMATION FOR SEQ ID NO:19:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:19:

YGAATCCTGY AAVGCTARRT DAATTGCTTG TAA 33

( 2 ) INFORMATION FOR SEQ ID NO:20:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:20:

YTGTGARTCT GTYACTATRT TTACTTCTRR TCC 33

( 2 ) INFORMATION FOR SEQ ID NO:21:

( i ) SEQUENCE CHARACTERISTICS:

( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:21:

TATTATTTGA YTRAC W A W CT CTGATTCACT YTK 33

( 2 ) INFORMATION FOR SEQ ID NO:22:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:22:

CAGRTARACY TTTTCCTTTT TTATTARYTG YTC 33

( 2 ) INFORMATION FOR SEQ ID NO:23:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:23:

TCCTCCAATY CCTTTRTGTG CTGGTACCCA TGM 33

( 2 ) INFORMATION FOR SEQ ID NO:24:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:24:

TCCHBBACTG ACTAATYTAT CTACTTGTTC ATT 33

( 2 ) INFORMATION FOR SEQ ID NO:25:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:25:

ATCTATTCCA TYYAAAAATA GYAYYTTYCT GAT 33

( 2 ) INFORMATION FOR SEQ ID NO:26:

( i ) SEQUENCE CHARACTERISTICS:
( A ) LENGTH: 33 nuuleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:26:

GTGGYAGRTT AAARTCAYTA GCCATTGCTY TCC 33

( 2 ) INFORMATION FOR SEQ ID NO:27:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:27:

CACAGCTRGC TACTATTTCY TTYGCTACYA YRG 33

( 2 ) INFORMATION FOR SEQ ID NO:28:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:28:

RYTGCCATAT YCCKGGRCTA CARTCTACTT GTC 33

( 2 ) INFORMATION FOR SEQ.ID NO:29:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:29:

DGAT W AYTTT TCCTTCYARA TGTGTACAAT CTA 33

( 2 ) INFORMATION FOR SEQ ID NO:30:

( i ) SEQUENCE CHARACTERISTICS:
( A ) LENGTH: 33 nuuleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:30:

CTATRTAKCC ACTRGCYACA TGRACTGCTA CYA 33

( 2 ) INFORMATION FOR SEQ ID NO:31:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:31:

CYTGYCCTGT YTCTGCTGGR ATDACTTCTG CTT 33

( 2 ) INFORMATION FOR SEQ ID NO:32:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:32:

TGSKGCCATT GTCTGTATGT AYTRYTKTTA CTG 33

( 2 ) INFORMATION FOR SEQ ID NO:33:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECLTLE TYPE: other nucleic acid ( x i ) SEQUENCE DESCRIPTION: SEQ ID NO:33:

GAATKCCAAA TTCCTGYTTR ATHCCHGCCC ACC 33

( 2 ) INFORMATION FOR SEQ ID NO:34:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:34:

ATTCYAYTAC YCCTTGACTT TGGGGRTTGT AGG 33

( 2 ) INFORMATION FOR SEQ ID NO:35:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:35:

GBCCTATRAT TTKCTTTAAT TCHTTATTCA TAG 33

( 2 ) INFORMATION FOR SEQ ID NO:36:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:36:

CTSTCTTAAG RTGYTCAGCY TGMTCTCTTA CYT 33

( 2 ) INFORMATION FOR SEQ ID NO:37:

( i ) SEQUENCE CHARACTERISTICS:
( A ) LENGTH: 33 nuclbotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:37:

TAAAATTGTG RATRAAYACT GCCATTTGTA C W G 33

( 2 ) INFORMATION FOR SEQ ID NO:38:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:38:

CTGCACTGTA YCCCCCAATC CCCCYTYTTC TTT 33

( 2 ) INFORMATION FOR SEQ ID NO:39:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:39:

TGTCTGT W GC TATYATRYCT AYTATTCTYT CCC 33

( 2 ) INFORMATION FOR SEQ ID NO:40:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:40:

TTRTRATTTG YTTTTGTART TCTYTARTTT GTA 33

( 2 ) INFORMATION FOR SEQ ID NO:41:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:41:

CATCTGCTCC TGTRTCTAAT AGAGCTTCYT TTA 33

( 2 ) INFORMATION FOR SEQ ID NO:42:

( i ) SEQUENCE CHARACTERISTICS:
( A ) LENGTH: 33 nuuieotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:42:

ATCCATYCCT GGCTTTAATT TTACTGGTAC AGT 33

( 2 ) INFORMATION FOR SEQ ID NO:43:

-continued ( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:43:

TATTCCTAAY TGRACTTCCC ARAARTCYTG AGT 33

( 2 ) INFORMATION FOR SEQ ID NO:44:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:44:

AC W YTGGAAT ATYGCYGGTG ATCCTTTCCA YCC 33

( 2 ) INFORMATION FOR SEQ ID NO:45:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:45:

CCATTTRTCA GGRTGGAGTT CATAMCCCAT CCA 33

( 2 ) INFORMATION FOR SEQ ID NO:46:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:46:

CTAYTATGGG KTCYKTYTCT AACTGGTACC AYA 33

( 2 ) INFORMATION FOR SEQ ID NO:47:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:47:

ATCTGGTTGT GCTTGAATPA TYCCYARTGC ATA 33

( 2 ) INFORMATION FOR SEQ ID NO:48:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear -continued ( i i ) MOLECULE TYPE: other nucleic acid ( x i ) SEQUENCE DESCRIPTION: SEQ ID NO:48:

CATGCATGGC TTCYCCTTTT AGYTGRCATT TAT 33

( 2 ) INFORMATION FOR SEQ ID NO:49:

( i ) SEQUENCE CHARACTERISTICS:
( A ) LENGTH: 33 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:49:

AACAGGCDGC YTTAACYGYA GYACTGGTGA AAT 33

( 2 ) INFORMATION FOR SEQ ID NO:50:

( i ) SEQUENCE CHARACTERISTICS:
( A ) LENGTH: 33 nucleotides
( B ) TYPE: nucleic acid
( C ) STRANDTDNESS: single
( D ) TOPOLOGY: linear ( i i ) MOLECULE TYPE: other nucleic acid ( x i ) SEQUENCE DESCRIPTION: SEQ ID NO:50:

TGTCYCTGTA ATAAACCCGA AAATTTTGAA TTT 33

( 2 ) INFORMATION FOR SEQ ID NO:51:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:51:

AGGCATAGGA CCCGTGTCTT 20

( 2 ) INFORMATION FOR SEQ ID NO:52:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:52:

CTTCTTTGGA GAAAGTGGTG 20

What is claimed:

1. A method for separating a pellet area from a supernatant in a centrifugation step in a nucleotide hybridization assay, wherein said method comprises:

(a) providing a liquid sample containing a target nucleic acid;

(b) adding a bead to said liquid sample, wherein said bead is not bound to an antibody;

(c) centrifuging said liquid sample to form a supernatant and pellet, wherein said pellet comprises said bead;

(d) identifying the pellet area by the presence of said bead; and (e) removing the supernatant from the pellet area.

2. The method of claim 1, wherein said bead is colored.

3. The method of claim 2, wherein a plurality of beads are added to said liquid sample.

4. The method of claim 3, wherein the diameter of said beads is substantially between 0.1 μm and 1 μm.

5. The method of claim 4, wherein the density of said beads is substantially between 1.01 and 1.09 g/ml.

6. The method of claim 5, wherein said beads comprise polystyrene.

7. The method of claim 6, wherein said liquid sample comprises target nucleic acids having substantial sequence identity to a viral sequence selected from the group consisting of human immunodeficiency virus (HIV), hepatitis B virus (HBV), hepatitis C virus (HCV), human T-cell leukemia virus-1, and cytomegalovirus (CVM).

8. The method of claim 6, wherein the sample comprises target nucleic acids having substantial sequence identity to a genomic sequence from the group consisting of Chlamydia and *Mycobacteria tuberculosis.*

9. A centrifuged pellet for a nucleotide hybridization assay comprising a bead and a covalently linked target nucleic acid.

10. A pellet of claim 9, wherein said bead is colored.

11. A pellet of claim 10, wherein said pellet comprises a plurality of beads.

12. A pellet of claim 11, wherein the diameter said beads are substantially between 0.1 μm to 1 μm.

13. The pellet of claim 12, wherein said target nucleic acid having substantial sequence identity to a viral sequence selected from the group consisting of human immunodeficiency virus (HIV), hepatitis B virus, hepatitis C virus (HCV), human T-cell leukemia virus-1, and cytomegalovirus (CMV).

14. The pellet of claim 12, wherein said target nucleic acids having substantial sequence identity to a genomic sequence from the group consisting of Chlamydia and *Mycobacteria tuberculosis.*

* * * * *